United States Patent [19]
Pinnavaia et al.

[11] Patent Number: 5,840,264
[45] Date of Patent: *Nov. 24, 1998

[54] CRYSTALLINE INORGANIC OXIDE COMPOSITIONS PREPARED BY NEUTRAL TEMPLATING ROUTE

[75] Inventors: Thomas J. Pinnavaia; Peter T. Tanev, both of East Lansing, Mich.

[73] Assignee: Board of Trustees operating Michigan State University, East Lansing, Mich.

[ * ] Notice: The term of this patent shall not extend beyond the expiration date of Pat. No. 5,712,402.

[21] Appl. No.: 355,979

[22] Filed: Dec. 14, 1994

Related U.S. Application Data

[63] Continuation-in-part of Ser. No. 293,806, Aug. 22, 1994, abandoned.

[51] Int. Cl.$^6$ .................................................. C01B 33/20
[52] U.S. Cl. ...................... 423/277; 423/279; 423/327.1; 423/327.2; 423/328.1; 423/328.2; 423/328.3; 423/329.1; 423/331; 423/326; 423/593; 423/594; 423/595; 423/598; 423/600
[58] Field of Search ................................... 423/332, 333, 423/278, 279, 327.1, 327.2, 328.1, 328.2, 328.3, 329.1, 331, 326, 335, 593, 594, 595, 598, 600, 604, 606, 607, 608, 610, 618, 622, 624, 625, 632, 633, 634, 635

[56] References Cited

U.S. PATENT DOCUMENTS

| | | | |
|---|---|---|---|
| 3,702,886 | 11/1972 | Argauer et al. | 423/328 |
| 3,709,979 | 1/1973 | Chu | 423/328 |
| 4,108,881 | 8/1978 | Rollmann et al. | 423/328 |
| 4,151,189 | 4/1979 | Rubin et al. | 423/329 |
| 4,391,785 | 7/1983 | Rosinski et al. | 423/328 |
| 4,504,681 | 3/1985 | Armor | 502/323 |
| 4,619,820 | 10/1986 | Valyocsik | 423/328 |
| 4,910,006 | 3/1990 | Zones et al. | 423/328 |
| 5,057,296 | 10/1991 | Beck | 423/277 |
| 5,098,684 | 3/1992 | Kresge et al. | 423/277 |
| 5,102,643 | 4/1992 | Kresge et al. | 423/328 |
| 5,143,879 | 9/1992 | Whitehurst | 423/328 |

OTHER PUBLICATIONS

Kirk Othmer, Third Edition, vol. 2, pp. 627–631 (1978) No Month.
Gesser et al., "Aerogels and Related Porans Materials" *Chemical Reviews* vol. 89 No. 7, 1989 pp. 765–787 (no month).
Meier, et al., Atlas of Zeolite Structure Types, Butterworth, London, 451–456 (1992) (no month).
Barrer, et al., Zeolites, vol. 1, 130–140 (1981) Oct.
Davis, et al., Chem. Mater., vol. 4, 756–768 (no month) (1992).
Gies, et al., Zeolites, vol. 12, 42–49 (1992) Jan.
Hearmon et al, Zeolites, vol. 10, 608–611 (1990) Jul.
Davis, et al., Nature, vol. 331, 698–699 (1988) (No month).
Estermann, M., et al., Nature, vol. 352, 320–323 (1991) Jul.
Huo et al., J. Chem. Soc., Chem. Commun., 875–876 (1992) No month.

Soghmonian et al., Angew. Chem., Int. Ed. Engl., vol. 32, 610–611 (1993) (no month).

Beck et al., J. Am. Chem. Soc., vol. 114, 10834–10843 (1992) (no month).

Inagaki et al., J. Chem. Soc. Chem. Commun., vol. 8, 680–682 (1993) (no month).

Stucky et al., Nature, vol. 368, 317–321 (1994).

Pinnavaia et al., Nature, vol. 368, 321–323 (1994) Mar.

Sing et al., Pure Appl. Chem., vol. 57, 603–619 (1985) no month.

Perspectives in Molecular Sieve Science, Eds. Flank, W. H. and White, T.E. Jr., ACS Symposium Series No. 368, Wash.D.C., pp. 247: 524; 544 (1988) Jun.

Gunnawardane et al., Zeolites, vol. 8, 127–131 Mar. (1988).

Davis, et al., XIII North American Meeting of the Catalysis Soc., Book of Abstracts, p.D14 (1993) No month.

Coustel et al., J. Chem. Soc., Chem. Commun. 967–968 (1994) No Month.

Sachtler, W.M.H., Catal. Today 15, 419–429 (1992) No Month.

G. Horvath and K. J. Kawazoe, J. Chem. Eng. Jpn., 16, 470–475 (1983) (no month).

Sing et al., J. Chem. Soc., Chem. Commun., 1257–1258 (1993) No Month.

Chauvin et al., J. Catal., vol. 111, 94–105 (1988) (No Month).

Cartlidge et al., Zeolites, vol. 9, 346–349 (1989) Jul.

*Primary Examiner*—Michael Lewis
*Assistant Examiner*—Stuart L. Hendrickson
*Attorney, Agent, or Firm*—Ian C. McLeod

[57] ABSTRACT

This invention relates to new crystalline organic compositions having unique combinations of framework-confined uniform mesopores and textural mesopores and to a method for their preparation. The compositions typically possess a framework wall thickness of at least about 17 Å, small elementary particle size of less than about 400 Å, and ratio of textural to framework-confined mesoporosity of greater than about 0.2. The formation of the mesoporous structure is accomplished by a novel self-assembly mechanism involving hydrogen bonding between neutral amine surfactant (S°) and neutral inorganic oxide precursor (I°). This S°I° templating approach allows for facile and environmentally benign recycling of the cost-intensive template by simple solvent extraction methods.

4 Claims, 9 Drawing Sheets

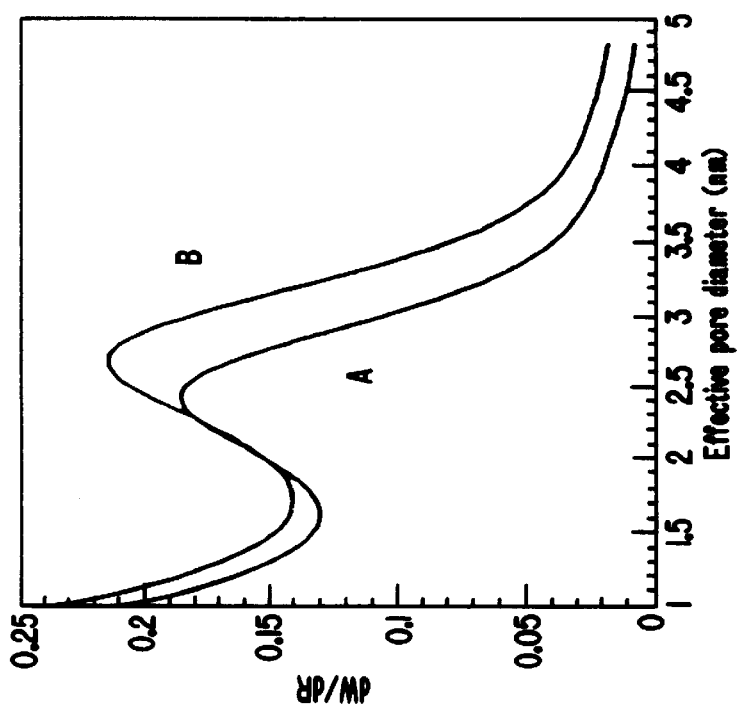
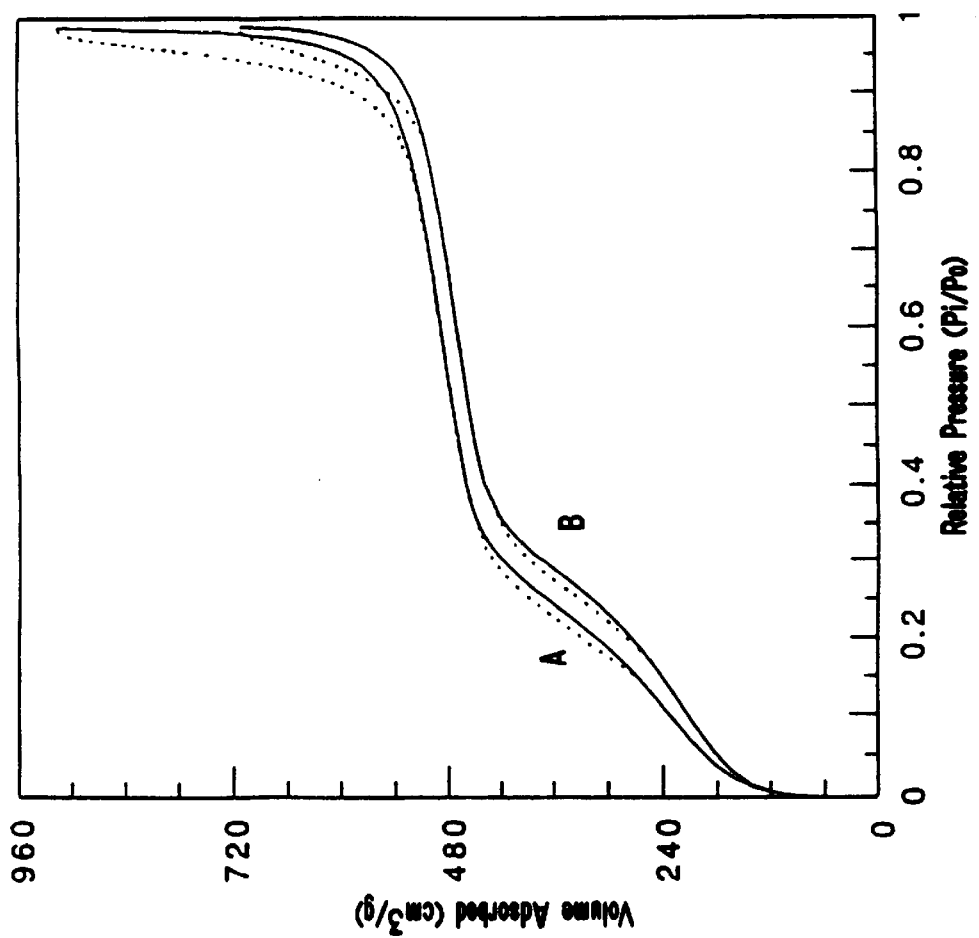
FIG. 4B
FIG. 4A

CRYSTALLINE INORGANIC OXIDE COMPOSITIONS PREPARED BY NEUTRAL TEMPLATING ROUTE

CROSS-REFERENCE TO RELATED APPLICATION

This application is a continuation-in-part of pending U.S. application Ser. No. 08/293,806, filed Aug. 22, 1994 now abandoned.

U.S. GOVERNMENT RIGHTS

The invention described in this application was sponsored by the National Science Foundation Contract CHE-9224102. The U.S. Government has certain rights to this invention.

BACKGROUND OF THE INVENTION (1) Field of the Invention

This invention relates to a new crystalline inorganic oxide compositions having framework wall thickness of at least about 17 Å, unique combinations of framework-confined uniform mesopores and textural mesopores, and small elementary particle size ($\leq 400$ Å). In particular, the present invention relates to such compositions formed by a novel self-assembly method comprising steps of hydrogen (H) bonding between neutral amine template (S°) and neutral inorganic oxide precursor (I°), followed by hydrolysis and crosslinking under mild reaction conditions. This invention also relates to a route for facile recovery and recycling of the template by simple solvent extraction.

(2) Description of Related Art

Porous solids created by nature or by synthetic design have found great utility in all aspects of human activity. The pore structure of the solids is usually formed in the stages of crystallization or subsequent treatment. Depending on their predominant pore size, the solid materials are classified as: (i) microporous, having pore sizes <20 Å; (ii) macroporous, with pore sizes exceeding 500 Å; and (iii) mesoporous, with intermediate pore sizes between 20 and 500 Å. The use of macroporous solids as adsorbents and catalysts is relatively limited due to their low surface area and large non-uniform pores. Microporous and mesoporous solids, however, are widely used in adsorption, separation technology and catalysis. Owing to the need for higher accessible surface area and pore volume for efficient chemical processes, there is a growing demand for new highly stable mesoporous materials. Porous materials can be structurally amorphous, paracrystalline, or crystalline. Amorphous materials, such as silica gel or alumina gel, do not possess long range order, whereas paracrystalline solids, such as γ- or η-$Al_2O_3$ are quasi ordered as evidenced by the broad peaks on their X-ray diffraction patterns. Both classes of materials exhibit a broad distribution of pores predominantly in the mesoporous range. This wide pore size distribution limits the shape selectivity and the effectiveness of the adsorbents, ion-exchanges and catalysts prepared from amorphous and paracrystalline solids.

The only class of porous materials possessing rigorously uniform pore sizes is that of zeolites and related molecular sieves. Zeolites are microporous highly crystalline aluminosilicates. Their lattice is composed by $IO_4$ tetrahedra (I=Al and Si) linked by sharing the apical oxygen atoms. Their pore network, which is confined by the spatially oriented $IO_4$ tetrahedra, consists of cavities and connecting windows of uniform size (Breck D. W., *Zeolite Molecular Sieves: Structure, Chemistry and Use*; Wiley and Sons; London, 1974). Because of their aluminosilicate composition and ability to discriminate small molecules, zeolites are considered as a subclass of molecular sieves. A non-zeolitic molecular sieves are crystalline framework materials in which Si and/or Al tetrahedral atoms of a zeolite lattice are entirely or in part substituted by other I atoms such as B, Ga, Ge, Ti, V, Fe, or P.

Zeolite frameworks are usually negatively charged due to the replacement of $Si^{4+}$ by $Al^{3+}$. In natural zeolites this charge is compensated by alkali or alkali earth cations such as $Na^+$, $K^+$ or $Ca^{2+}$. In synthetic zeolites the charge can also be balanced by quaternary ammonium cations or protons. Synthetic zeolites and molecular sieves are prepared usually under hydrothermal conditions from aluminosilicate or phosphate gels. Their crystallization, according to the hereafter discussed prior art, is accomplished through prolonged reaction in an autoclave for 1–50 days and, often times, in the presence of structure directing agents (templates). The proper selection of template is of extreme importance for the preparation of a particular framework and pore network. A large variety of organic molecules or assemblies of organic molecules with one or more functional groups are known in the prior art to give more than 85 different molecular sieve framework structures. (Meier et al., *Atlas of Zeolite Structure Types*, Butterworth, London, 1992). Excellent up to date reviews of the use of various organic templates and their corresponding structures, as well as the mechanism of structure directing are given in Barrer et al., *Zeolites*, vol. 1, 130–140 (1981); Lok et al., *Zeolites*, vol. 3, 282–291 (1983); Davis et al., *Chem. Mater.*, vol. 4, 756–768 (1992) and Gies et al., *Zeolites*, vol. 12, 42–49 (1992). For example, U.S. Pat. No. 3,702,886 teaches that crystallization of aluminosilicate gel (high Si/Al ratio) in the presence of quaternary tetrapropyl ammonium hydroxide template affords zeolite ZSM-5. Other publications teaching the use of various organic directing agents include, for example, U.S. Pat. No. 3,709,979, wherein quaternary cations, such as tetrabutyl ammonium or tetrabutyl phosphonium, are used to crystallize zeolite ZSM-11 and U.S. Pat. No. 4,391,785 demonstrating ZSM-12 preparation in the presence of tetraethyl ammonium cations. Another zeolite-ZSM-23 synthesis, directed by $(CH_3)_3N^+(CH_2)_7N^+(CH_3)_3$ dications, is taught in U.S. Pat. No. 4,619,820. The use of yet another dicationic template-N, N, N, N', N', N', -hexamethyl-8,11-[4.3.3.0] dodecane diammonium diiodide, for the preparation of zeolite SSZ-26, is shown in U.S. Pat. No. 4,910,006.

Other prior art teaches that primary amines such as propylamine, i-propylamine (U.S. Pat. No. 4,151,189), and diamines, such as diaminopentane, diaminohexane and diaminododecane (U.S. Pat. No. 4,108,881) also direct the synthesis of the ZSM-5 type structure. However, as pointed out by Hearmon et al., *Zeolites*, vol. 10, 608–611 (1990), it is the protonated form of these amines which most likely is responsible for the framework assembly.

In summary, most of the prior art zeolites and molecular sieve frameworks were assembled by using quaternary ammonium cations or protonated forms of amines or diamines as templates.

The search for new organic directing agents, as evident in the increasing number of prior art reports, is attributable to: (i) the need for new and attractive types of stable frameworks and (ii) to the need for expanding the uniform micropore size to mesopore region and thus allowing one to adsorb, process and discriminate among much larger molecules. However, the prior art molecular sieves typically possess uniform pore size in the microporous region. This pore size is predetermined by the thermodynamically favored formation of framework windows containing 8, 10 and 12 -I atom rings. Thus, the ability of the prior art zeolites and molecular sieves to adsorb, process and discriminate among molecules of certain shape and size is strictly limited by the size of these windows. During the last three decades considerable synthetic effort has been devoted to developing frameworks with pore sizes larger than that of the naturally occurring zeolite faujasite (pore size 7.4 Å). However, due to the above limitations, the synthetic faujasite analogs, zeolite X or Y, with 8 Å pore windows (Breck D. W., *Zeolite Molecular Sieves: Structure, Chemistry and Use*; Wiley and Sons; London, 1974), maintained for decades their position as the largest pore molecular sieves. The replacement of aluminosilicate gels by alumino—and gallophosphate gels gave new direction to the synthesis of large uniform pore materials. Thus, a 18-membered ring aluminophosphate molecular sieve VPI-5 (Davis et al., *Nature*, vol. 331, 698–699 (1988)), was found to possess a structure with an hexagonal arrangement of one-dimensional channels (pores) of diameter≈12 Å. The discovery of a 20-membered ring gallophosphate molecular sieve-cloverite, exhibiting a uniform pore size of 13 Å is disclosed in Estermann M. et al., *Nature*, vol. 352, 320–323 (1991). Recently, Thomas et al., *J. Chem. Soc., Chem. Commun.*, 875–876 (1992) reported a triethyl ammonium cation-directed synthesis of a novel 20-membered ring aluminophosphate molecular sieve, denoted JDF-20, having uniform pore size of 14.5 Å (calculated from lattice parameters). Very recently, a preparation of vanadium phosphate with 18.4 Å lattice cavity was disclosed in Soghmonian et al., *Angew. Chem., Int. Ed. Engl.*, vol. 32, 610–611 (1993). However, the actual pore size of these two materials is unknown since sorption data are lacking. In summary, in spite of the significant progress made toward the preparation of large pore size materials, all of the above mentioned molecular sieves still possess uniform pore size in the microporous region.

A breakthrough toward the preparation of mesoporous molecular sieves have been disclosed recently in U. S. Pat. Nos. 5,098,684; 5,102,643. The claimed class of mesoporous materials (denoted as M41S) of this prior art was found to possess uniform and adjustable pore size in the range of 13–100 Å. In addition, these materials exhibited a small framework wall thickness of from 8 to 12 Å and elementary particle size of usually much above 500 Å. Depending on preparation conditions M41S materials with hexagonal (MCM-41), cubic (MCM-48) or layered crystallographic structure have been disclosed (Beck et al., *J. Am. Chem. Soc.*, vol. 114, 10834–10843 (1992). The postulated mechanism of formation of these materials involves strong electrostatic interactions and ion pairing between quaternary ammonium liquid crystal cations, as structure directing agents, and anionic silicate oligomer species (U.S. Pat. No. 5,098,684). Related mesoporous structures also have been prepared by rearrangement of a layered silicate (kanemite) (Inagaki et al., *J. Chem. Soc. Chem. Commun.*, vol. 8, 680–682 (1993)) in the presence of quaternary ammonium cations. Recently, Stucky et al. (*Nature*, vol. 368, 317–321 (1994)) extended the electrostatic assembly approach by proposing four complementary synthesis pathways. Pathway 1 involved the direct co-condensation of anionic inorganic species (I$^-$) with a cationic surfactant (S$^+$) to give assembled ion pairs (S$^+$I$^-$), the original synthesis of MCM-41 being the prime example (U.S. Pat. No. 5,098,684). In the charge reversed situation (Pathway 2) an anionic template (S$^-$) was used to direct the self-assembly of cationic inorganic species (I$^+$) via S$^-$I$^+$ ion pairs. The pathway 2 has been found to give a hexagonal iron and lead oxide and different lamellar lead and aluminum oxide phases (Stucky et al., ibid). Pathways 3 and 4 involved counterion (X$^-$ or M$^+$) mediated assemblies of surfactants and inorganic species of similar charge. These counterion-mediated pathways afforded assembled solution species of type S$^+$X$^-$I$^+$ (e. g., X$^-$=Cl$^-$, Br$^-$) or, S$^-$M$^+$I$^-$ (e.g., M$^+$=Na$^+$, K$^+$), respectively. The viability of Pathway 3 was demonstrated by the synthesis of a hexagonal MCM-41 using a quaternary ammonium cation template and strongly acidic conditions (5–10M HCl or HBr) in order to generate and assemble positively-charged framework precursors (Stucky et al., ibid). In another example, a condensation of anionic aluminate species was accomplished by alkali cation mediated (Na$^+$, K$^+$) ion pairing with an anionic template ($C_{12}H_{25}OPO_3$). The preparation of the corresponding lamellar Al(OH)$_3$ phase in this case has been attributed to the fourth pathway (S$^-$M$^+$I$^-$). Also, we have reported (Pinnavaia et al., *Nature*, vol. 368, 321–323 (1994)) the preparation of a mesoporous silica molecular sieve and a Ti-substituted analogue by the acid catalyzed hydrolysis of inorganic alkoxide precursors in the presence of primary ammonium ions produced by the acid.

Since all of the above pathways are based on charge matching between ionic organic directing agents and ionic inorganic reagents, the template is strongly bonded to the charged framework and difficult to recover. In the original Mobil approach (U.S. Pat. No. 5,098,684) the template was not recovered, but simply burned off by calcination at elevated temperatures. Recently, it has been demonstrated that the ionic surfactant in Pathway 1 materials could be removed by ion-exchange with acidic cation donor solution (U.S. Pat. No. 5,143,879). Also, the template-halide ion pairs in the framework of acidic Pathway 3 materials were displaced by ethanol extraction (Stucky et al., ibid). Thus, ionic template recovery is possible, provided that exchange ions or ion pairs are present in the extraction process.

While water molecules are easily removed by heating and evacuation, the quaternary ammonium cations, due to their high charge density, are strongly bonded or confined to the pore cavities and channels of the negatively charged framework. The same concepts are expected to apply for the charge reversed situation were an anionic template is confined in the pores of a positively-charged framework. Therefore, a cation or anion donor or ion pairs are necessary in order to remove the charged template from the framework of the prior art molecular sieves.

Textural porosity is the porosity that can be attributed to voids and channels between elementary particles or aggregates of such particles (grains). Each of these elementary particles in the case of molecular sieves is composed of certain number of framework unit cells or framework-confined uniform pores. The textural porosity is usually formed in the stages of crystal growth and segregation or subsequent thermal treatment or by acid leaching. The size of the textural pores is determined by the size, shape and the number of interfacial contacts of these particles or aggregates. Thus, the size of the textural pores is usually at least one or two orders of magnitude larger than that of the framework-confined pores. For example, the smaller the particle size, the larger the number of particle contacts, the smaller the textural pore size and vice versa. One skilled in the art of transmission electron spectroscopy (TEM) can determine the existence of framework-confined micropores from High Resolution TEM (HRTEM) images or that of framework-confined mesopores from TEM images obtained by observing microtomed thin sections of the material as taught in U.S. Pat. No. 5,102,643.

One skilled in the art of adsorption could easily distinguish and evaluate framework-confined uniform micropores by their specific adsorption behavior. Such materials usually give a Langmuir type (Type I) adsorption isotherm without a hysteresis loop (Sing et al., *Pure Appl. Chem.*, vol. 57, 603–619 (1985)). The existence of textural mesoporosity can easily be determined by one skilled in the art of SEM, TEM and adsorption. The particle shape and size can readily be established by SEM and TEM and preliminary information concerning textural porosity can also be derived. The most convenient way to detect and assess textural mesoporosity is to analyze the $N_2$ or $Ar_2$ adsorption-desorption isotherm of the solid material. Thus, the existence of textural mesoporosity is usually evidenced by the presence of a Type IV adsorption-desorption isotherm exhibiting well defined hysteresis loop in the region of relative pressures Pi/Po>0.4 (Sing et al., *Pure Appl. Chem.*, vol. 57, 603–619 (1985)). This type of adsorption behavior is quite common for a large variety of paracrystalline materials and pillared layered solids.

The microporous zeolites and molecular sieves of the prior art exhibit mainly framework-confined uniform micropores, and no textural mesoporosity as evidenced by their Langmuir type adsorption isotherms without hysteresis loops at Pi/Po>0.4 and the large crystalline aggregate size of >2 μm, more usually from 5 to 20 μm. The typical values for their specific surface area are from 300–800 m$^2$/g and for the total pore volume $\leq 0.6$ cm$^3$/g (Perspectives in *Molecular Sieve Science*, Eds. Flank, W. H. and White T. E. Jr., ACS symposium series No. 368, Washington D. C., p. 247; 524; 544 (1988)). Most of these structures are prepared by prolonged crystallization at hydrothermal conditions, using quaternary ammonium cations or protonated primary, secondary or tertiary amines to assemble the anionic inorganic species into a framework. It should also be noted that the use in the prior art of neutral amines and alcohols as templates (Gunnawardane et al., *Zeolites*, vol. 8, 127–131 (1988)) has led to the preparation of only microporous highly crystalline (particle size >24 μm) molecular sieves that lack appreciable textural mesoporosity. For the mesoporous molecular sieves of the MCM-41 family the uniform mesopores are also framework-confined. This has been verified by TEM lattice images of MCM-41 shown in U.S. Pat. No. 5,102,643. Therefore, the framework of this class of materials can be viewed as a expanded version of a hexagonal microporous framework. The existence of these framework-confined uniform mesopores was also confirmed by the capillary condensation phenomenon observed in their adsorption isotherms. Typical $N_2$ adsorption-desorption isotherm of MCM-41 (Davis et al., *XIII North American Meeting of the Catalysis Soc., Book of Abstracts*, p. D14 (1993)) is included here for reference (FIG. 1). This adsorption isotherm is essentially the same as that obtained previously by Sing et al., *J. Chem. Soc., Chem. Commun.*, 1257–1258 (1993). The isotherm is constituted by sharp adsorption uptake followed by a hysteresis loop in the Pi/Po region of 0.3 to 0.4. This hysteresis corresponds to capillary condensation into the framework-confined uniform mesopores. The lack of appreciable hysteresis beyond Pi/Po>0.4 implies the absence of textural mesoporosity. This lack of textural mesoporosity is also supported in some cases by the highly ordered hexagonal prismatic shaped aggregates of size>2 μm (Beck et al., *J. Am. Chem. Soc.*, vol. 114, 10834–10843 (1992). The total pore volume of the material reported by Davis et al. is ≈0.7 cm$^3$/g and that of the framework-confined mesopores, as determined from the upper inflection point of that hysteresis loop, is almost equal to that of the total pore volume. Therefore, the ratio of textural to framework-confined mesoporosity here approaches zero. The size of the framework-confined uniform mesopores is ≈30 Å.

In summary, the crystalline molecular sieve materials of the aforementioned prior art typically lack appreciable textural mesoporosity. However, there is increasing number of reports in the literature suggesting that textural mesopores behave as a transport pores to the framework-confined uniform pores and that they greatly improve the access and the performance of adsorbents, ion-exchangers and catalysts. This, for example, is demonstrated in Pinnavaia et al., *Nature*, vol. 368, 321–323 (1994); Chavin et al., *J. Catal.*, vol. 111, 94–105 (1988) and in Cartlidge et al., *Zeolites*, vol. 9, 346–349 (1989). According to this prior art the transport pores provide more efficient assess to the framework-confined pores of the zeolite.

In summary, the prior art molecular sieve materials, as well as their preparation approaches have the following disadvantages:

1. The prior art uses charged surfactant ions (S$^+$ or S$^-$) as templates in order to assemble an inorganic oxide framework from charged inorganic precursors (I$^-$ or I$^+$). This charged templates are usually expensive, strongly bonded to the charged inorganic oxide framework and difficult to recover. In addition, some charged templates, such as quaternary ammonium ions are highly toxic and, therefore, potential health hazards. In all the prior art examples the electrostatically bonded templates were removed from the framework by either a burning off process or by an ion-exchange reaction with an ion donor solution. Also, ion pairs were necessary in order to extract the template from the framework of pathway 3 materials.

2. Yet other important disadvantages of the prior art mesoporous molecular sieves are the small framework wall thickness (from 8 to 12 Å), large elementary particle size (typically much above 500 Å) and the absence of an optimal balance of framework-confined and textural mesoporosity. This deficiency is attributable to the strong electrostatic interactions and the specific preparation conditions governing their self-assembly process. This does not contribute to improving the thermal stability, the textural mesoporosity and to accessing the framework-confined uniform mesopores. The lack of textural mesoporosity could lead to serious diffusion limitations in many potential applications. The ratio of textural to the framework-confined mesoporosity of these materials is usually close to zero.

The aforementioned disadvantages of this prior art severely limit the practical use of these crystalline materials.

Therefore, there is a need for new, templated, inorganic oxide structures with large framework wall thickness, small particle size and complementary framework-confined and textural mesoporosity. Also there is a need for a new preparation art to these ordered mesostructures which would allow for cost reduction by employing less expensive reagents and mild reaction conditions while at the same time providing for the effective recovery and recyclability of the template.

OBJECTS

An object of the present invention is to provide a new S° I° approach to the design of crystalline, inorganic oxide compositions with high thermal stability (large framework wall thickness), containing balanced uniform framework-confined mesoporosity and textural mesoporosity and small elementary particle size $\leq 400$ Å.

Another subject of the present invention is to provide inexpensive preparation methods for these materials by avoiding the use of charged ionic templates and charged inorganic oxide precursors and high temperature hydrothermal synthesis conditions.

Still another object of this invention is to provide for the facile recovery and recycling of the template by new separation art involving simple solvent extraction from the crystalline product.

These and other objects will become increasingly apparent from the following description and the drawings.

BRIEF DESCRIPTION OF THE DRAWINGS

FIG. 4 is a $N_2$ adsorption (-) and desorption (- -) isotherms for the product of Example 2 (curve A) and for the product B of Example 5 (curve B). FIG. 4B The corresponding Horvath-Kawazoe framework-confined mesopore size distribution curves.

DESCRIPTION OF PREFERRED EMBODIMENTS

Figure 1:
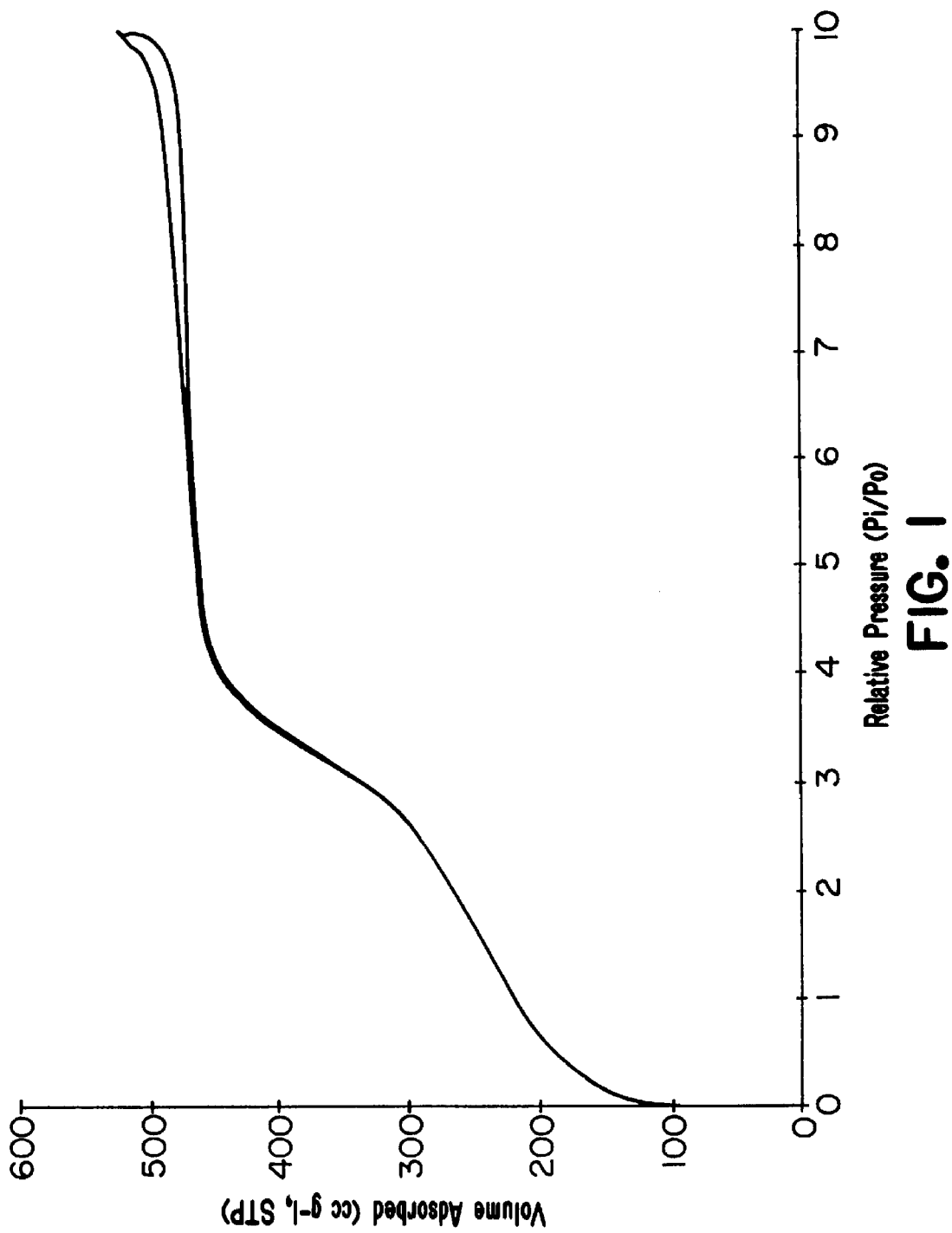
FIG. 1 is a representative $N_2$ adsorption-desorption isotherm for the prior art MCM-41 product from Davis et al., *XIII North American Meeting of the Catalysis Soc.*, Book of Abstracts, p. D14 (1993).

The present invention relates to a crystalline inorganic oxide composition having large framework wall thickness ($\geq 17$ Å), a unique combinations of framework-confined mesoporosity and textural mesoporosity, and small elementary particle size ($\leq 400$ Å) prepared by a neutral S° I° self-assembly mechanism. This novel templating mechanism comprises reacting a neutral amine template solution and neutral inorganic oxide precursor solution to form a reaction product, hydrolysis of the reaction product, and the subsequent removal of the aqueous solution and the template. This invention is broader than the silicate compositions described in Ser. No. 08/293,806, filed Aug. 22, 1994.

A new templating route to mesoporous molecular sieves that is complementary to Pathways 1 to 4 of the prior art is disclosed. Our approach is based on H-bonding and self-assembly between neutral primary amine micelles (S°) and neutral inorganic precursors (I°). This new S° I° templating route, which we denote Pathway 5, affords mesostructures with larger wall thicknesses, small particle sizes and complementary textural mesoporosities relative to Pathway 1 and 3 materials. The thicker pore walls are highly desired as improving the thermal and hydrothermal stability (Coustel et al., *J. Chem. Soc., Chem. Commun.*, 967–968 (1994)) of the mesopore framework. The small particle size and substantial textural mesoporosity are essential for accessing the framework-confined pores and for improving the performance of the obtained adsorbents and catalysts (Pinnavaia et al., ibid; Chavin et al., *J. Catal.*, vol. 111, 94–105 (1988)). In addition, the S° I° pathway allows for facile recovery of the template by simple solvent extraction circumventing the need for cation donors or ion pairs to remove the charged template.

Hereafter, we define and differentiate the terms framework-confined uniform porosity and textural porosity. Framework-confined uniform pores are pores formed by nucleation and crystallization of the framework elementary particles. These pores typically are cavities and channels confined by the solid framework. The size of the cavities and channels, i.e. the size of the framework-confined uniform pores, in molecular sieve materials is highly regular and predetermined by the thermodynamically favored assembly routes. The framework-confined pores of freshly crystallized product are usually occupied by the template water molecules and water.

The present invention relates to a method for the preparation of a synthetic, crystalline inorganic oxide or substituted inorganic oxide composition comprising: (a) preparing a solution of a neutral inorganic oxide precursor (I°), containing at least one di-, tri-, tetra-, penta- or hexavalent element or mixture thereof; and optionally aging the said I° inorganic oxide precursor solution under stirring at a temperature of at least minus 20° C. for at least 5 minutes; (b) preparing a homogeneous solution of neutral amine template in a hydrolyzing agent, and optionally a co-solvent by stirring it at temperature between about minus 20° and plus 100° C.; mixing of the solutions of steps (a) and (b) at a temperature between about minus 20° and plus 100° C. to form a gel which is aged for at least about 30 minutes to form the crystalline product; separating at least some of the hydrolyzing agent from the crystalline product, preferably with air drying or template removal; and optionally calcining the crystalline product at about 300° to 1000° C. for at least about 30 minutes.

The present invention also relates to a neutral S°I° synthetic route for the preparation of a crystalline inorganic oxide compositions comprising: (a) preparing an aged solution of at least one neutral inorganic oxide precursor with stirring at a temperature of at least minus 20° C. for at least 5 minutes (aging is optional); (b) preparing a homogeneous solution of a neutral amine template with a hydrolyzing agent and co-solvent (optional) with stirring at a temperature between about minus 20° C. and plus 100° C.; mixing of the solutions of steps (a) and (b) at a temperature between about minus 20° C. and plus 100° C. to form a gel which is aged for at least about 30 minutes or longer to form a crystalline product; separating at least some of the hydrolyzing agent from the crystalline product, preferably with air drying or separating the template; and optionally calcining the crystalline product at 300° to 1000° C. for at least about 30 minutes.

The present invention provides a new class of inorganic oxide crystalline materials with thicker framework walls, complementary framework-confined uniform and textural mesopores and typically small elementary particle size that can be used as an adsorbents and catalysts for the catalytic conversion of organic substrates. This new class of materials is distinguished from the prior art materials by possessing larger framework wall thickness of $\geq 17$ Å, typically very small elementary particle size $\leq 400$ Å, significant amount of textural mesoporosity, and a ratio of textural to framework-confined mesoporosity typically $\geq 0.2$.

In addition, the crystalline inorganic oxide compositions of the present invention are obtained by a new S°I° neutral preparative method. According to the preparation art of this invention the formation of the mesoporous structures is accomplished primarily by H-bonding between a neutral template and a neutral inorganic oxide precursors, followed by further hydrolysis and crosslinking of $IO_m$ units, where I is a central metallic or non-metallic element coordinated to m oxygen atoms ($2 \leq m \geq 8$). This H-bonding most likely occurs between any I—OH or I-proton donor compound, and the lone pair of electrons on the central atom of the template head group. Specifically, the said method comprises the formation of a gel by mixing of a neutral template solution with a neutral inorganic oxide precursor, preferably a inorganic alkoxide or a neutral inorganic oxide sol, in the presence of hydrolyzing agent and a co-solvent (optional), followed by aging and crystallization under stirring at temperature of at least minus 20° C. for at least 0.5 h. Much of the template can be recovered by extraction of the templated product with water or with alcohol, or a mixture thereof, or by vacuum distillation, more preferably by extraction with alcohol. Complete removal of the last traces of template and the further crosslinking of the $IO_m$ framework is accomplished by calcination at 300° to 1000° C.

Applicants are unaware of prior art teaching the present crystalline compositions of inorganic oxide molecular sieve materials having large framework wall thickness of $\geq 17$ Å, complementary framework-confined uniform mesoporosity and textural mesoporosity and small elementary particle size ($\leq 400$ Å). Also, applicants know of no prior art teaching the preparation of these compositions by a neutral $S°I°$ mechanism involving H-bonding between neutral amine template and neutral inorganic oxide precursor, hydrolysis and crystallization at mild reaction conditions and template recovery and recycling by solvent extraction of the templated product.

This result is achieved by using neutral templates to assemble a neutral reactant precursors into a mesoporous framework structure, while at the same time increasing the framework wall thickness and limiting crystal growth in most cases to a range where complementary textural mesoporosity is achieved. Hydrogen bonding between the template and the reagent is the primary driving force of the framework assembly process of this invention. Here a neutral amine plays the role of both a solvent and template for the neutral precursor. Water plays a role of hydrolyzing reagent and the alcohol acts as co-solvent.

The molar ratio of amine to inorganic oxide precursor in the initial reaction mixture is between about 0.05 and 3, preferably about 0.25 and about 1.4. The crystalline inorganic oxide composition of the present invention preferably has in its as-synthesized and anhydrous state the following formula:

$$nR/K_xL_yM_zN_pO_q$$

wherein R is at least one neutral amine or diamine such as dodecyl amine or 1,12-diamine dodecane; K is optional and is at least one divalent element such as Mg, Zn or Cu; L is optional and at least one trivalent element such as B, Al, Ga, Cr or Fe; M is optional and is at least one tetravalent element such as Si, Ge, Ti, V, or Zr; N is optional and is at least one pentavalent or hexavalent element such as V, W or Mo; O is oxygen and n, x, y, z, p and q are the molar parts of R, K, L, M, N and O, respectively. In the calcined composition n is preferably 0, x is preferably between 0.001 and 1; y is between 0.001 and 2; z is between 0.001 and 1; p is between 0.001 and 2 and q is between 1 and 6.

The crystalline mesoporous materials of this invention may be characterized as formed by H-bonding between neutral inorganic oxide precursors containing I—OH groups as hydrogen donors and a neutral amine templates as hydrogen acceptors, followed by further hydrolysis and crosslinking of $IO_m$ units under mild reaction conditions. This H-bonding occurs between any I—OH or generally any I-proton donor group in which the I-inorganic atom is coordinated to m groups capable of participating in a H-bonding with the lone pair of electrons on the central atom of the head group of the neutral organic template. Specifically, the method comprises formation of a gel by mixing of a neutral amine template solution with a solution of at least one inorganic oxide alkoxide or neutral inorganic oxide sol or gel precursor in the presence of a hydrolyzing agent and a co-solvent (optional), followed by hydrolysis, aging and crystallization under stirring at temperature of at least minus 20° C. for at least 0.5 h. More particularly, the calcined composition of this invention is characterized by at least one strong X-ray diffraction peak at a d-spacing of at least 15 Å or greater. The said compositions are distinguished in part from prior art MCM-41 materials by a substantially larger framework wall thickness ($\geq 17$ Å) and a much smaller elementary particle size $\leq 400$ Å. More specifically, the crystalline composition of this invention may be distinguished from those of prior art, including MCM-41 materials, by the presence of complimentary textural mesoporosity. A distinctive feature of the present compositions is that the ratio of textural to framework-confined mesoporosity can be varied in the range from about 0.2 to 10 by careful selection of the neutral amine template and the reaction conditions. Thus, by varying the textural to framework-confined mesoporosity ratio one can mediate the accessibility of the pore structure of the crystalline product, depending on the demands of the particular application.

The said compositions can be used as an adsorbents, ion-exchangers or a catalysts. According to this invention the removal of the template from the reaction product can be achieved by at least four ways: (i) air drying followed by calcination in air or in inert gas at temperature from 300°–1000° C. for 30 min to 72 h; (ii) solvent extraction of the templated product; and (iii) by vacuum distillation of the product; (iv) by various combinations of (i) to (iii). The fact that the template can be recycled by non-ionic recovery methods (ii) and (iii) is also a distinctive feature of this invention. Procedure (i) results in the destruction of the template. The separation of the template by extraction or distillation should be followed by air drying and calcination in air or inert gas to remove the final traces of template and to complete the crosslinking of the mesostructure.

After template removal and calcination, the said material can be used as an adsorbent for non-polar or polar organic molecules or as a gas drying agent. Furthermore, the said calcined product when framework substituted, or subsequently impregnated, as taught in Sachtler, W. M. H., Catal. Today 15, 419–429 (1992), with proper amount of catalytically active element, such as Al, Ti, V, Pt, Pd, Cu, Cr or mixture thereof, or when immobilized with transition inorganic macrocycles, could be used as a catalyst for cracking, hydrocracking, hydrogenation-dehydrogenation, isomerization or redox reactions involving organic substrates.

The new preparation method of the composition of this invention involves the preparation of solutions comprising sources of di-, tri-, tetra-, penta- or hexavalent elements, or mixture thereof, a solvent (optional), aging and reacting this solution with template solution at mild reaction conditions, under stirring, until formation of the desired crystalline product and recovering the crystalline material. The said template, can be described more particularly as a neutral (non-ionic) molecule of formula $R_1R_2R_3N$, wherein N is nitrogen and at least one of $R_1$, $R_2$ and $R_3$ is selected from the group of alkyl of from 6 to 22 carbon atoms or aryl of from 6 to 18 carbon atoms or combination thereof. The remaining R groups are selected from the group consisting of hydrogen or alkyl from 1 to 22 carbon atoms or combination thereof. In addition, said material successfully can be synthesized in the presence of neutral diamines of formula $R_1R_2N$—X—$NR_4R_5$ wherein X is selected from the group of alkyl, aryl or combination thereof from 1 to 18 carbon atoms and the remaining R groups are selected from the group consisting of hydrogen, alkyl and aryl of from 1 to 18 carbon atoms or combination thereof.

Preferred reaction mixtures for the typical preparation of the composition of this invention have the following oxide molar ratio ranges:

| Reagents | Useful | Preferred |
|---|---|---|
| KO/R | 0.3 to 10 | 0.6 to 5 |
| $L_2O_3$/R | 0.25 to 10 | 0.5 to 5 |
| $MO_2$/R | 0.5 to 20 | 0.5 to 5 |
| $NO_q$/R | 0.3 to 10 | 0.6 to 5 |
| $H_2O$/R | 10 to 800 | 20 to 250 |
| Co-solvent/$H_2O$ | 0 to 5 | 0 to 2 | wherein R is at least one neutral amine or diamine such as dodecyl amine or 1,12-diamine dodecane; K is optional and is at least one divalent element such as Mg, Zn or Cu; L is optional and at least one trivalent element such as B, Al, Ga, Cr or Fe; M is optional and is at least one tetravalent element such as Si, Ge, Ti, V, or Zr; N is optional and is at least one pentavalent or hexavalent element such as V, W or Mo; O is oxygen and n, x, y, z, p and q are the molar parts of R, K, L, M, N and O, respectively. In the calcined composition n is preferably 0, x is preferably between 0.001 and 1; y is between 0.001 and 2; z is between 0.001 and 1; p is between about 0.001 and 2 and q is between 1 and 6.

The preparation procedures of the said compositions comprise steps as follows:

(i) Preparing a solution of neutral inorganic oxide precursor of a di-, tri -, tetra-, penta- or hexavalent element or mixture thereof in the presence (optional) of hydrolyzing agent and/or co-solvent.

(ii) Aging the inorganic oxide precursor solution under stirring for at least 5 min at a temperature of at least minus 20° C. for at least 5 minutes (optional).

(iii) Preparing a homogeneous solution of the neutral template in a hydrolyzing agent or in hydrolyzing agent and co-solvent.

(iv) Reacting the inorganic oxide precursor solution with the template solution by stirring at a temperature from minus 20° C. to plus 100° C.

(v) Aging the resulting gel under stirring at the desired temperature for at least 30 min.

(vi) Air drying the product and/or separating the template by either extraction with water or alcohol or a mixture thereof, or by distillation of the templated product. After template removal the product is subjected to calcination to remove trace amounts of template and to complete the crosslinking of the framework.

(vii) Calcining the product at 300° to 1000° C. in air or inert gas for at least 30 min.

Herein said inorganic oxide solutions are prepared from neutral precursors such as the silicates of Ser. No. 08/293,806, filed Aug. 22, 1994 and such as alkoxides, inorganic hydrocarbons such as silanes, or inorganic complexes which upon hydrolysis afford a I—OH species. The list of preferred alkoxides include, in particular, aluminum(III) tri-ethoxide, aluminum(III) isopropoxide, aluminum(III) n-, tert- or sec-butoxide, antimony(III) isopropoxide, antimony(III) n-butoxide, calcium(II) ethoxide, calcium(II) isopropoxide, calcium(II) tert-butoxide, chromium(IV) tert-butoxide, chromium(III) isopropoxide, copper(II) methoxyethoxide, gallium(III) isopropoxide, germanium(IV) ethoxide, germanium(IV) isopropoxide, indium(III) isopropoxide, iron(III) ethoxide, iron(III) tert-butoxide, iron(III) isopropoxide, lead(II) isopropoxide, lead(II) tert-butoxide, magnesium(II) ethoxide, molybdenum(V) isopropoxide, manganese(II) isopropoxide, niobium(V) ethoxide, strontium(II) isopropoxide, tetramethyl orthosilicate, tetraethyl orthosilicate (TEOS), tetrapropyl orthosilicate, tetrabutyl orthosilicate, tetrahexyl orthosilicate, $H[OSi(OC_2H_5)_2]_nOH$ where n=4–6, $RSi(OR)_3$, tin(IV) isopropoxide, tetraethyl orthotitanate, tetrapropyl orthotitanate, tetraisopropyl orthotitanate (TIPOT), tetrabutyl orthotitanate, tetraoctadecyl orthotitanate, tungsten(VI) ethoxide, tungsten(VI) isopropoxide, vanadium(V) triisopropoxide oxide, zinc(II) isopropoxide, zinc(II) tert-butoxide, zirconium(IV) n-propoxide, zirconium(IV) isopropoxide, zirconium(IV) tert-butoxide or mixtures thereof. Also a variety of a neutral colloidal inorganic oxide precursor solutions or inorganic oxide gels also can be used to prepare the compositions of the present invention. For example, a potential sources of a neutral silica include the variety of commercially available fumed silicas or silica gels.

Said co-solvent (optional) is selected from the group of normal or isomerized alcohols having 1 to 12 carbon atoms and at least one OH group, such as methanol, ethanol, propanol, butanol, hexanol, octanol, dodecanol. More preferably, said co-solvent is an ethanol, propanol, 2-propanol or mixture thereof. Those skilled in the art will know that polyols in which more than one OH group is present also can be used as a co-solvent.

The said aging of the substituted inorganic oxide precursor solution is preferably performed at 60°–75° C. for 3 to 4 h.

The said template is a neutral primary, secondary or tertiary amine or polyamine or mixture thereof, preferably a primary amine or diamine, more preferably primary amine, having at least one alkyl chain of from 6 to 22 carbon atoms or mixture thereof.

Said reacting of the inorganic oxide precursor solution and template solution is preferably carried out at 20° to 45° C. by random order of reagent addition, more preferably by adding the inorganic oxide precursor solution to the stirred template solution. More specifically said reacting is performed by H-bonding between neutral inorganic oxide precursors and a neutral template, followed by further hydrolysis and crosslinking of $IO_m$ units at mild reaction conditions. This H-bonding most likely occurs generally between any I—OH or I-proton donor compound and the lone pair of electrons on the central atom of the head group of the organic template.

The said aging of the gel is accomplished preferably for 0.5–24 h, more preferably from 12 to 18 h.

Said calcinating is performed by heating in an oven at a temperature preferably from 300°–650° C. for 4 h.

The outstanding features of the present method are:

(i) The use of neutral templates (S°), particularly amines or diamines, to assemble the mesoporous framework structure;

(ii) The use of neutral inorganic oxide precursors (I°) such as alkoxides, inorganic hydrocarbons or inorganic oxide sols and gels as a sources of inorganic oxides.

(iii) The aging of the substituted inorganic oxide precursor solution at 60°–80° C. for 1–4 h in order to obtain polymerized I—O—I species.

(iv) The use of hydrogen bonding as a driving force for the neutral S°I° assembly process between the neutral template and neutral inorganic oxide precursor species;

(v) The use of mild reaction conditions to prepare the template ordered product;

(vi) The recovery and recycling of the template by a new separation art involving simple non-ionic solvent extraction or distillation from the product.

(vii) The use of a new inexpensive preparation art.

The templated inorganic oxide compositions of the present invention may be combined with other zeolites or clays or inorganic oxides or organic polymers or mixture thereof, in order to prepare adsorbents, ion-exchangers, catalysts, catalytic carriers or composite membranes with high thermal and mechanical resistance. In addition, one skilled in the art could impregnate said composition of the present invention or use it as an encapsulating agent for transition metal macrocycles such as phthalocyanines and porphyrins. The active phase in these cases could be a transition metal for example Cu, Co, Ni, Fe, Ti, V, W, Pt, Pd or Mo or mixtures thereof. These catalysts can be used in conversion such as catalytic cracking, hydrocracking, reforming, isomerization, dealkylation or oxidation in the presence or absence of $H_2O_2$ or $O_2$ or mixture thereof.

The following specific examples are intended to be illustrative of the present invention, but are not intended to limit the invention.

EXAMPLES 1–3

Thirty five milliliters of deionized $H_2O$ was mixed with 35 milliliters of ethanol (co-solvent is optional) under stirring and the appropriate amount of template (see Table 1) was added. The resultant mixture was stirred until a clear solution of template was obtained. A 13.66 gram—quantity of $Si(OC_2H_5)_4$ was added at once to the above solution of template. The reaction stoichiometry expressed in terms of moles per mole $SiO_2$ corresponded to the following:

0.26 or 0.27 moles $C_nH_{2n+1}NH_2$
29.6 moles $H_2O$
9.09 moles of EtOH.

The resulting gels were stirred and aged at ambient temperature for 18 h to obtain the templated products. The crystalline products were calcined at 630 ° C. for 4 h in order to remove the incorporated template.

The X-ray diffraction patterns of all samples were measured on a Rigaku Rotaflex diffractometer equipped with rotating anode and Cu—$K_\alpha$ radiation ($\lambda$=0.15148 nm). The diffraction data were recorded by step-scanning at 0.01 degrees of 2θ, were θ is the Bragg angle, and counting time of 1 sec per each step. The d-spacings of the X-ray reflections of the samples were calculated in Angstrom units (Å).

The elementary particle sizes and of all samples were obtained from the line width of the $d_{100}$ reflections on the XRD-patterns. The electron micrographs and the electron diffraction patterns of the samples were taken on a JEOL JEM-100CX II electron microscope by observing microtomed thin sections of the examined material, supported on carbon coated Cu grids (400 mesh). The sample images were obtained using an accelerating voltage of 120 kV, a beam diameter of ≈5 μm and an objective lens aperture of 20 μm. The electron diffraction patterns were recorded by using an accelerating voltage of 100 kV, a beam size of ≈5 μm and a diffraction aperture of 20 μm.

The pore structure of the said samples was characterized by measuring the $N_2$ adsorption-desorption isotherms on a Coulter Omnisorp 360 CX Sorptometer at −195° C. using standard continuous sorption procedures. Before the measurement, each sample was heated overnight at 150° C. and $10^{-6}$ Torr. The specific surface area ($S_{BET}$, m$^2$/g) and the total pore volume ($V_1$, cc/g) were calculated from the isotherms following the IUPAC recommendations (Sing et al., *Pure Appl. Chem.*, 57, 603–619 (1985)). The pore size distribution of the materials was calculated using the method of Horvath and Kawazoe (G. Horvath and K. J. Kawazoe, *J. Chem. Eng. Jpn.*, 16, 470–475 (1983)). The volume of pores corresponding to framework-confined uniform mesopores was evaluated from the upper inflection point of the low Pi/Po hysteresis loop and that of the textural mesopores by the formula $V_{textural} = V_{total} - V_{framework-confined}$.

The thermogravimetric analyses of all samples were performed on a CAHN system TG analyzer using heating rate of 5° C./min.

The specific amounts of surfactant used in each particular example together with the corresponding X-ray d-spacing of the most intense low angle reflection (100) of the calcined product are summarized in Table 1.

TABLE 1

| Example | Template chain length | Amount of template used (g) | $d_{100}$ (Å) | Crystalline Phase | Particle size (Å) | $a_o$* (Å) | HK pore size† (Å) | Wall thickness‡ (Å) |
|---------|----------------------|-----------------------------|---------------|-------------------|-------------------|------------|-------------------|---------------------|
| 1 | $C_8$ | 2.17 | 36 | Hexagonal | 110 | 42 | 16 | 26 |
| 2 | $C_{12}$ | 3.27 | 36 | Hexagonal | 170 | 42 | 24 | 18 |
| 3 | $C_{18}$ | 4.52 | 42 | Hexagonal | 145 | 48 | 31 | 17 |

* The repeat distance between pore centers of the hexagonal structure. This distance is calculated from the XRD data using the formula $a_o = 2d_{100}/\sqrt{3}$.

† The framework-confined mesopore size was determined by Horvath-Kawazoe (HK) analysis of the $N_2$ adsorption isotherm.

‡ The framework wall thickness is determined by subtracting the HK mesopore size from the repeat distance between pore centers.

The data in Table 1 reveal that our compositions possess much larger framework wall thickness (from 17 to 26 Å) than that reported in the aforecited prior art for MCM-41 materials (from 8 to 12 Å). Thus, our compositions are expected to possess a much higher thermal and hydrothermal stability than that observed for the MCM-41 materials.

Figure 2:
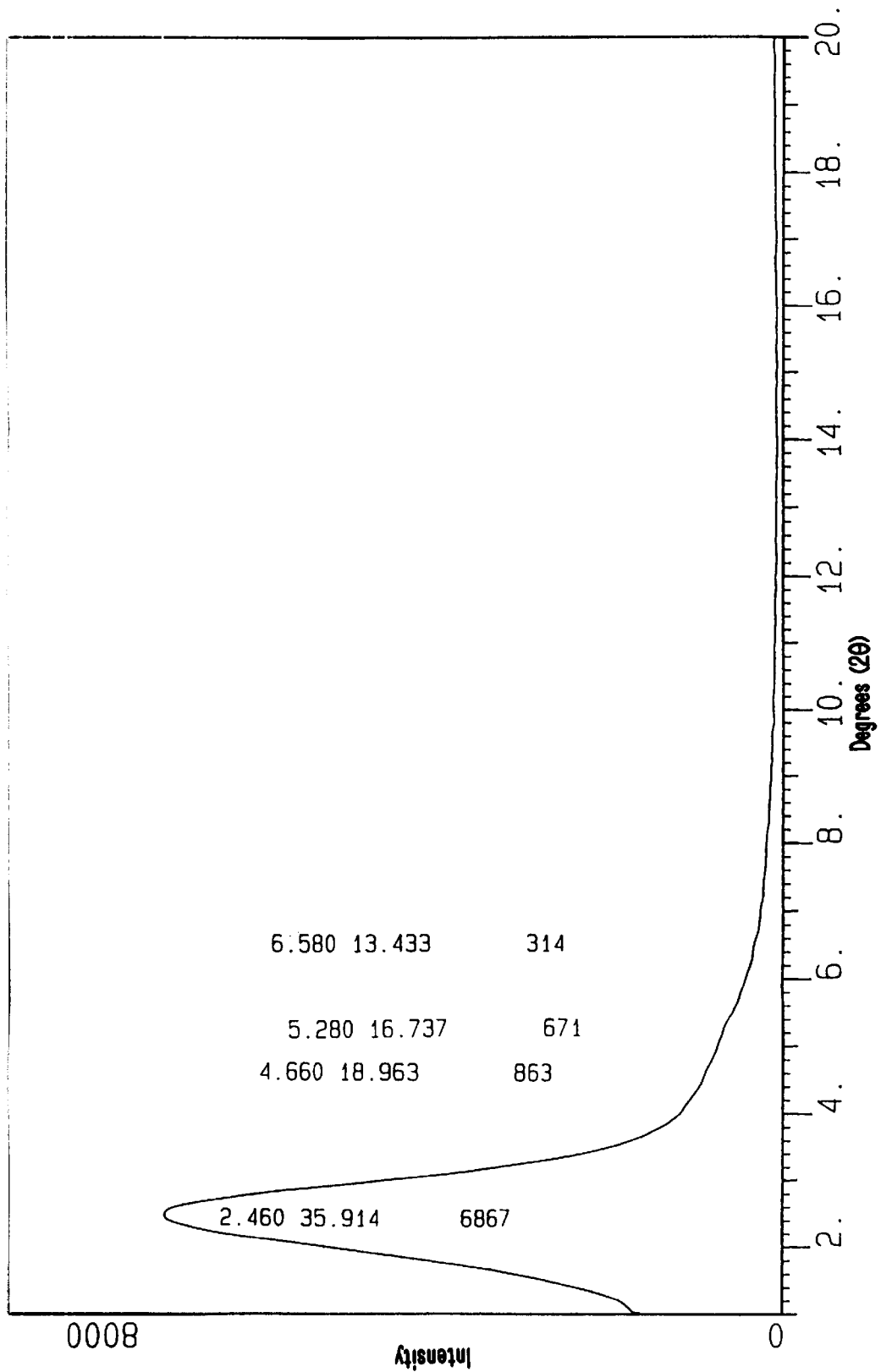
FIG. 2 is an X-ray powder diffraction pattern of the product of Example 2.
Figure 3:
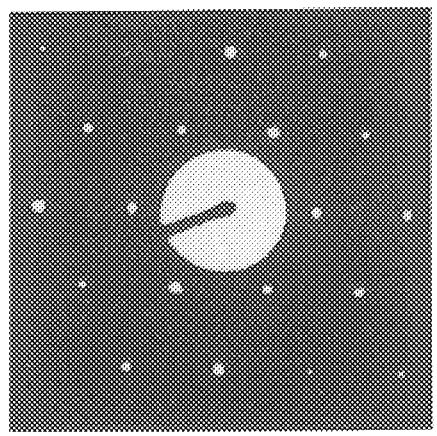
FIG. 3 is an electron diffraction pattern of the product of Example 2.

The X-ray diffraction pattern of the calcined product of Example 2 is shown in FIG. 2. It exhibits a strong relative intensity peak at 36±1.0 Å d-spacing and a diffuse scattering centered at ≈17.0±2.0 Å. The electron diffraction pattern of this product, presented as FIG. 3, shows typical hexagonal arrangement of the diffraction maxima similar to that observed for MCM-41 type materials by prior art (U.S. Pat. No. 5,098,684). The $N_2$ adsorption-desorption isotherm of the calcined product, shown in FIG. 4A curve A, is composed of two well defined hysteresis loops corresponding to the presence of complementary framework-confined and textural mesoporosity. The corresponding pore structure characteristics of the products of these examples are summarized in Table 2.

TABLE 2

| Example | Template chain length | $S_{BET}$ (m²/g) | $V_{total}$ (cc/g) | $V_{fr}$ (cc/g) | $V_{tex}$ (cc/g) | $V_{tex}/V_{fr}$ (cc/g) |
|---|---|---|---|---|---|---|
| 1 | $C_8$ | 1044 | 1.45 | 0.47 | 0.98 | 2.1 |
| 2 | $C_{12}$ | 1150 | 1.40 | 0.70 | 0.70 | 1.0 |
| 3 | $C_{18}$ | 763 | 0.73 | 0.62 | 0.11 | 0.2 |

The comparison of the data presented in Table 2 indicates that longer template alkyl chains afford smaller ratios of textural to framework-confined mesoporosity and vice versa. Thus, the variation in $V_{tex}/V_{fr}$ ratio for this particular oxide system was found to be from 2.1 to 0.2. However, for other oxide systems this ratio could vary from 0.2 to 10. This variation implies that the ratio of textural to framework-confined mesoporosity in our compositions can be tuned by careful selection of the neutral amine template chain length. This teaching is not apparent from the prior art synthetic strategies (U.S. Pat. Nos. 5,098,684, 5,102,643, and 5,057, 296).

EXAMPLE 4

In another example a solution containing 3.36 grams of a 1,12- diaminododecane template in 35 milliliters of deionized water and 35 milliliters of ethanol (co-solvent is optional) was obtained under vigorous stirring. A 13.66 gram-portion of $Si(OC_2H_5)_4$ was added at once to the above solution of template. Sixty milliliters of deionized $H_2O$ was added to the above mixture. The reaction stoichiometry expressed in terms of moles per mole $SiO_2$ corresponded to the following:

0.26 moles $C_nH_{2n}N_2H_4$
29.6 moles $H_2O$
9.09 moles of EtOH.

Figure 5:
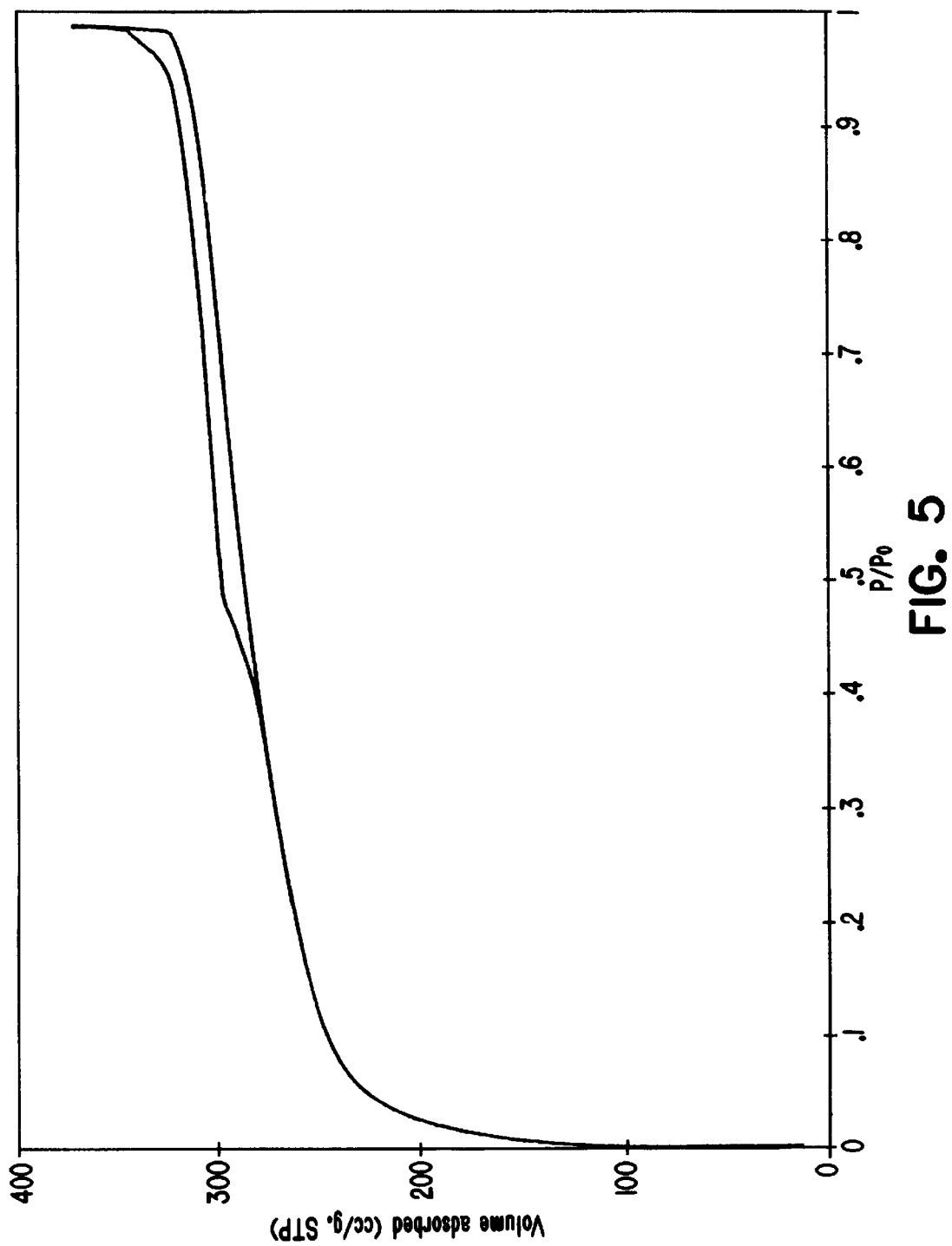
FIG. 5 is a $N_2$ adsorption-desorption isotherm of the calcined product of Example 4.

The resulting gel was aged at ambient temperature under vigorous stirring for 18 h to obtain the templated crystalline product. The product was calcined at 630° C. for 4 h in order to remove the incorporated template. The XRD pattern for this product exhibited a $d_{100}$ reflection centered at 24±1 Å. The nitrogen adsorption-desorption isotherm of this product is presented in FIG. 5. In contrast to the products of Examples 1–3 the calcined product of this Example (templated with neutral diamine) exhibits a different nitrogen sorption behavior. This is evidenced by the hysteresis loop of type H4 on the nitrogen sorption isotherm which is typical for layered materials (Sing et al., *Pure Appl. Chem.*, 57, 603–619 (1985)). In addition, the t-plot analysis of this product shows that the pore structure consists a complementary framework-confined microporosity and textural mesoporosity. The $S_{BET}$ of this sample is 969 m²/g and the total pore volume 0.51 cc/g.

EXAMPLE 5

The following experiment was chosen to exemplify the new template recovery art of the present invention.

Figure 6:
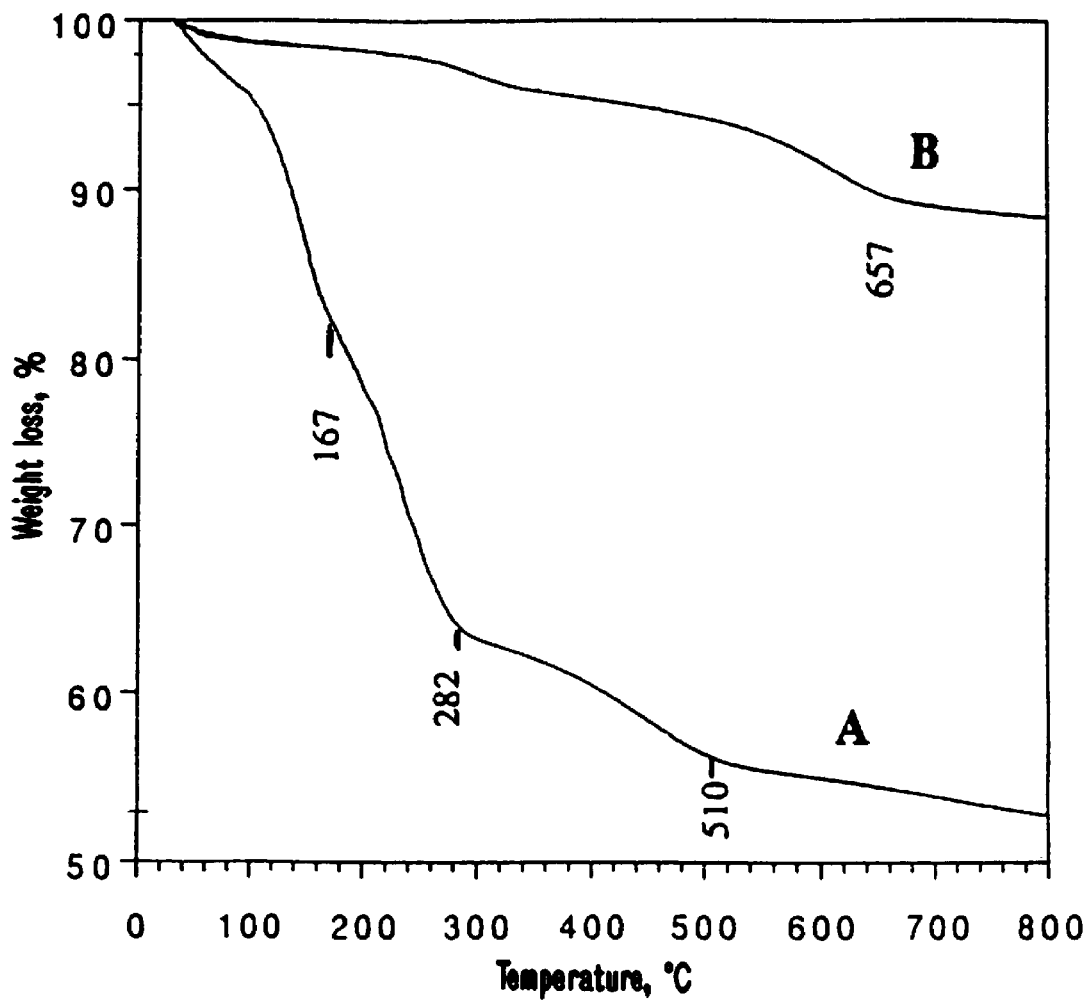
FIG. 6 are thermogravimetric curves of the product A (curve A) and product B (curve B) of Example 5.

(Product A) A 0.03 gram-quantity of the air-dried and non-calcined product of the Example 2 was subjected to thermogravimetric analysis (TGA) at heating rate 5° C./min. The corresponding weight loss curve is shown in FIG. 6A. The total weight loss of this sample is ≈46%. This curve is constituted of three distinguishable weight loss steps centered at temperatures of 167°, 282° and 510° C. which could be attributed to the loss of adsorbed water, desorption or decomposition of the template and dehydroxylation of the surface, respectively.

Figure 7:
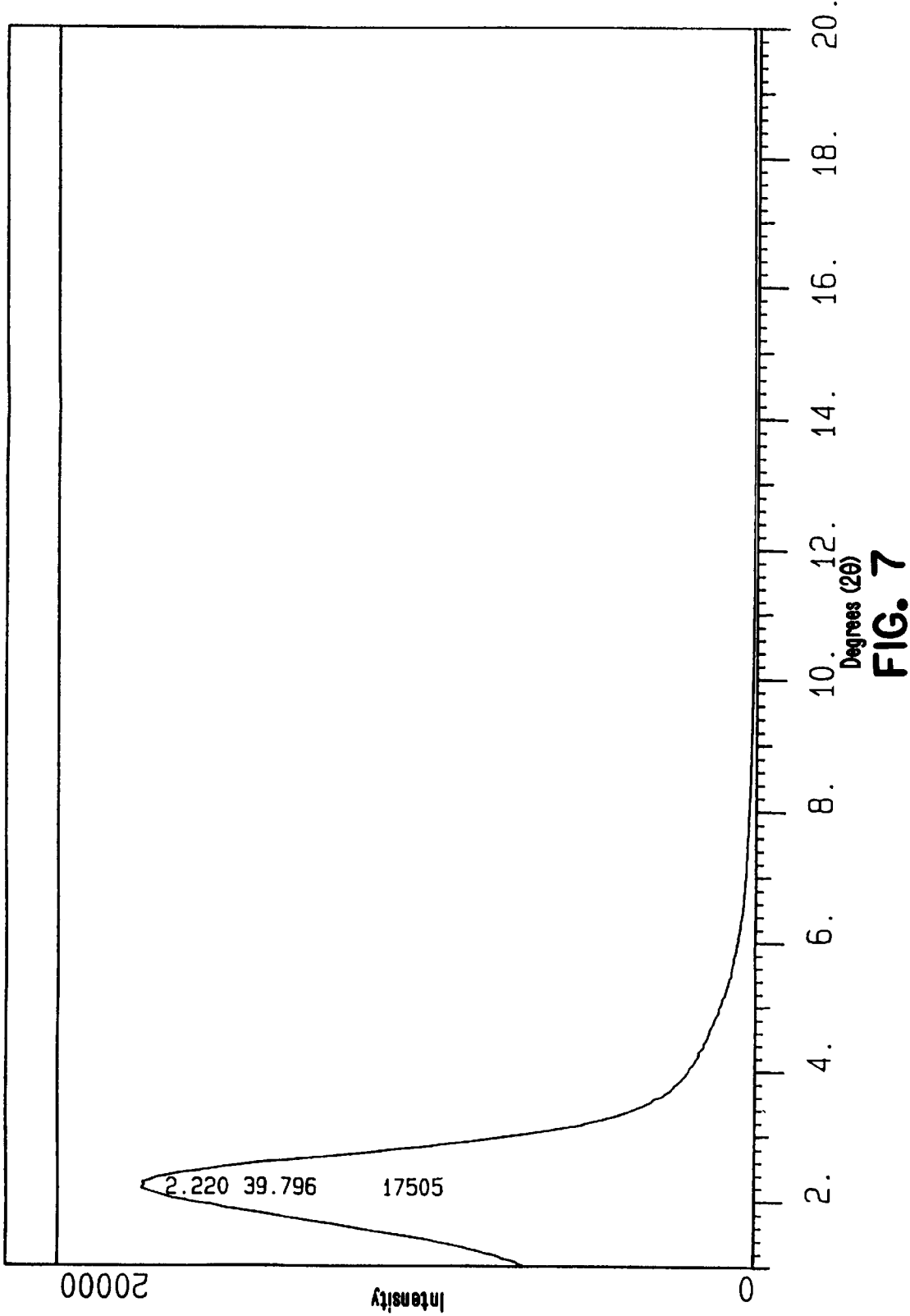
FIG. 7 is an X-ray powder diffraction pattern of the product B of Example 5.

(Product B) One gram of the air-dried and non-calcined product of Example 2 was mixed with 150 milliliters of EtOH, stirred and heated at 45°–75° C. for 30 min. The product was then filtered and washed with another portion of EtOH (100 milliliters) . The above washing procedure was repeated twice and the filtered product was air-dried at 80° C. The product was subjected to TGA analysis. The curve obtained is presented in FIG. 6B. In contrast to the TGA curve of product A that of product B reveals only about 11% total weight loss with ~9% corresponding to water desorption and dehydroxylation. The absence of amine was also confirmed by the absence of C—H stretching bands on the IR spectrum of the product. The X-ray diffraction pattern of the EtOH extracted product (FIG. 7) exhibits a $d_{100}$ reflection at 40±1 Å that is four times stronger than that observed for the calcined product A. The $N_2$ adsorption-desorption isotherm and the Horvath-Kawazoe pore size distribution of the ethanol-extracted product B are nearly identical to these for the calcined product A (compare curves A and B, FIGS. 4A and 4B). The specific surface area of both samples are also similar, namely, 1000 and 1150 m²/g. This demonstrates that the neutral (S°) template has been efficiently removed from the neutral (I°) framework of our inorganic compositions by ethanol extraction. The extracted organic template in the form of EtOH solution can be recycled and reused after simple concentration of the solution. In order to determine the thermal stability of the extracted product B we have performed a calcination in air at 450° C. for 7 hr. The X-ray analysis of the calcined product shows that the d-spacing spacing (41 Å) is retained even after such prolonged calcination.

EXAMPLE 6

A 3.27 gram-portion of dodecyl amine was dissolved in 50 milliliters of deionized $H_2O$ and 50 milliliters of ethanol under vigorous stirring. Twelve grams of LUDOX® SK, a 25% deionized colloidal silica solution in water, was added at once to the solution of template under vigorous stirring. Initially, a clear solution is obtained. The reaction stoichiometry expressed in terms of moles per mole $SiO_2$ corresponded to the following:

0.35 moles $C_nH_{2n+1}NH_2$
65.55 moles $H_2O$
17.04 moles of EtOH.

After 48 hr of aging at ambient temperature the solution transformed into a milk-like suspension of the templated crystalline product. The XRD pattern of the air-dried product exhibited a $d_{100}$ reflection centered at 37±1 Å.

EXAMPLE 7

In another example 2.8 gram-quantity of dodecyl amine was added to 50 milliliters of deionized $H_2O$ under stirring.

A 16.2 gram-portion of butanol (BuOH) was added to facilitate the dissolution of the template. Six grams of 80% Zr(i-BuO)$_4$ solution in buthanol was measured into a glass vial filled with 11.3 grams of BuOH, and the mixture slowly added to the solution of a template at ambient temperature under vigorous stirring. The reaction immediately formed a precipitate of the templated product. It should be noted that the rate of hydrolysis could be lowered significantly by performing the synthesis in an ice bath. The reaction mixture had the following composition in terms of moles per mole $ZrO_2$:

1.2 moles $C_nH_{2n+1}NH_2$ 221.4 moles $H_2O$ 31.0 moles of BuOH.

The obtained gel was aged at ambient temperature for 48 hr and the templated crystalline product was washed with water, filtered and air-dried on a glass plate. The air-dried material exhibited a $d_{100}$ reflection centered at 50±1 Å. The ethanol extracted product exhibited a $d_{100}$ reflection centered at 39±1 Å.

EXAMPLE 8

In another example a 3.27 gram-portion of dodecyl amine was dissolved in 35 milliliters of $H_2O$ and 35 milliliters of EtOH under vigorous stirring. Twenty grams of a Nalco TX-2146 R/S tin oxide sol was added slowly to the above clear solution of template. The reaction mixture had the following composition in terms of moles per mole $SnO_2$:

0.89 moles $C_nH_{2n+1}NH_2$ 145.12 moles $H_2O$ 30.0 moles of EtOH.

Figure 8:
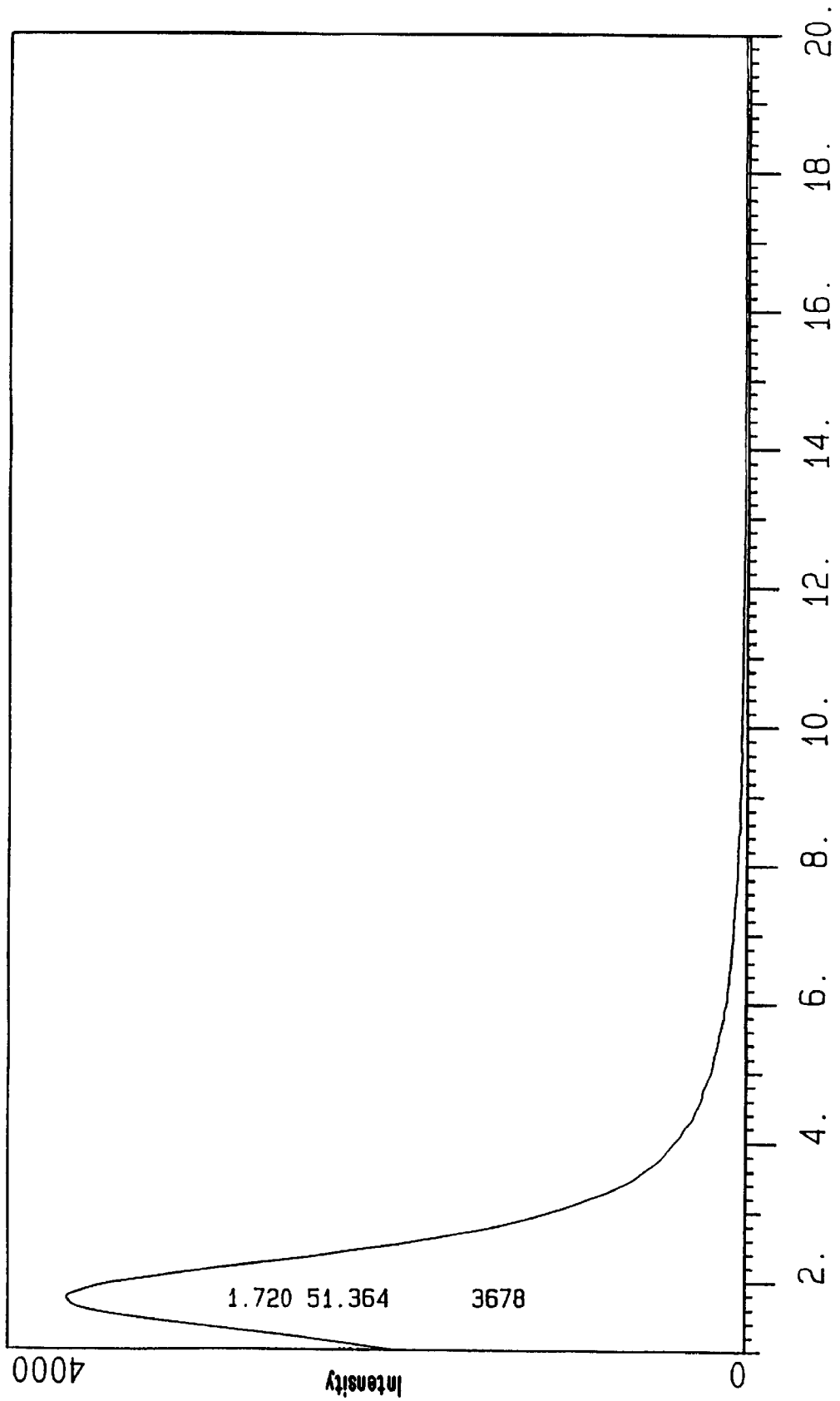
FIG. 8 is an X-ray powder diffraction pattern of the product of Example 8.

Within a few minutes the clear solution turned into a suspension containing the precipitated templated product. The powder diffraction pattern of the ethanol extracted product of this example is presented in FIG. 8. It is obvious that the templated $SnO_2$ mesostructure retains its crystallinity after template extraction ($d_{100}$=51 Å). Also, X-ray analysis of the calcined product (300° C. for 2 hr) of this example shows that the d-spacing of 51 Å is retained after calcination.

EXAMPLE 9

A 4.4 gram-quantity of octyl amine was mixed with 60 milliliters of deionized $H_2O$ and 35 milliliters of ethanol. Ten grams of Al(i-PrO)$_3$ was dissolved by heating (70° C.) and stirring in 50 milliliters of ethanol. The obtained clear hot aluminum i-propoxide solution was added to the solution of template under vigorous stirring at temperature of ≈50° C. The reaction mixture had the following composition in terms of moles per mole $Al_2O_3$:

1.4 moles $C_nH_{2n+1}NH_2$ 136.2 moles $H_2O$ 59.2 moles of EtOH.

Figure 9:
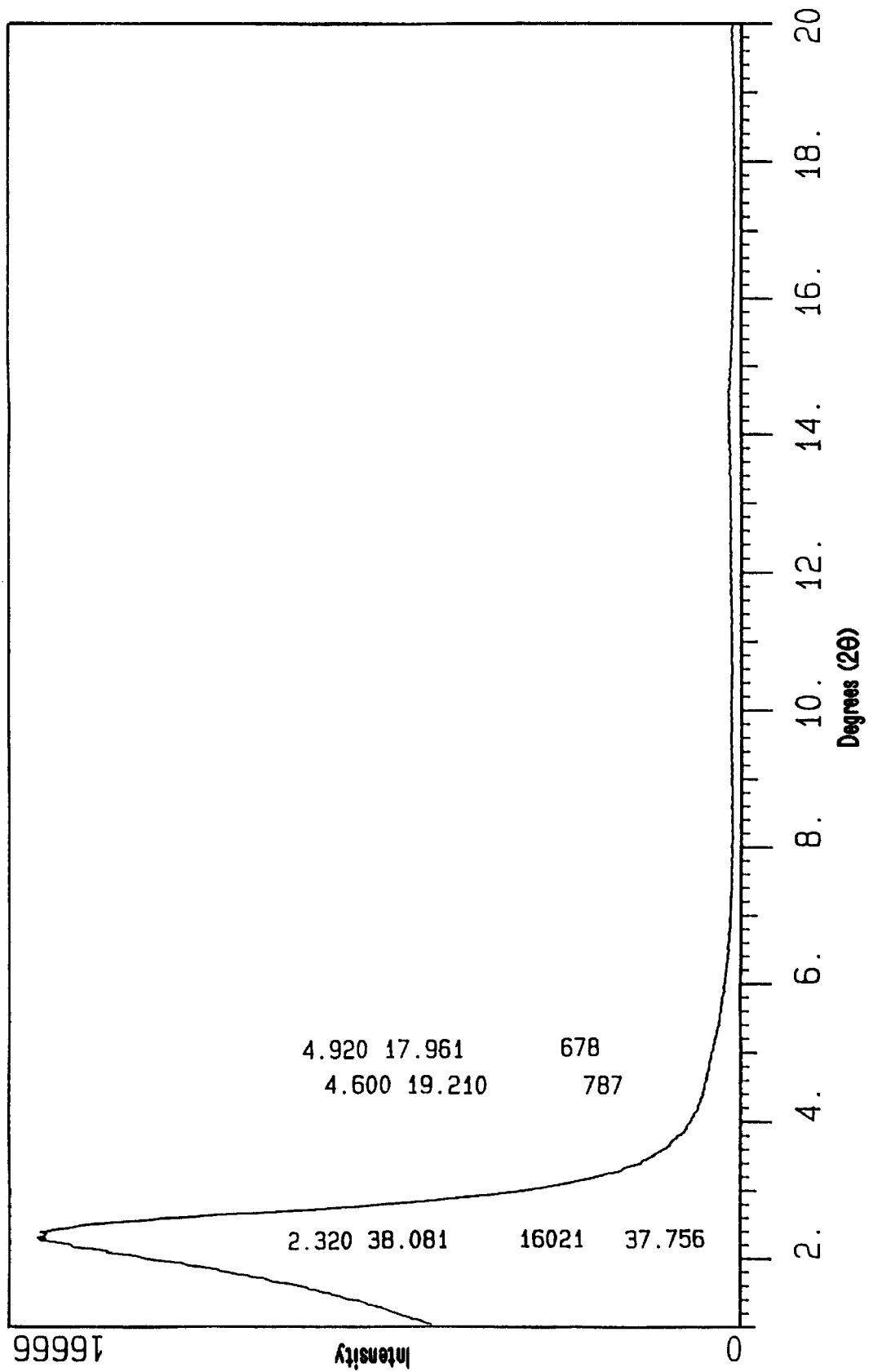
FIG. 9 is an X-ray powder diffraction pattern of the product of Example 9.

The resulting solution was kept at 50° C. for 1 hr and then aged in an open vessel at ambient temperature for 3 days to form the crystalline product. The powder diffraction pattern of the air-dried product of this example is presented in FIG. 9. The sample exhibits a typical hexagonal diffraction pattern as evidenced by the strong $d_{100}$ reflection at 38±1 Å and the diffuse scattering centered at approximately 18 Å. To the best of our knowledge this example illustrates the first successful preparation of a hexagonal templated alumina mesostructure. This disclosure can be expected to have a significant impact on the catalytic industry since substantially part of the industrially important heterogeneous catalysts are based on a quasi ordered alumina supports possessing non-uniform distribution of mesopores. The success of the preparation could be attributed to the herein disclosed novel S°I° templating approach to regular inorganic oxide mesostructures and to the much larger (in contrast to the prior art U.S. Pat. Nos. 5,098,684, 5,102,643, and 5,057,296) ratio of neutral template to neutral inorganic precursor employed for the preparation.

The foregoing description is only illustrative of the present invention and the present invention is limited only by the hereinafter appended claims.

We claim:

1. A calcined crystalline inorganic oxide composition having a framework wall defining uniform framework-confined mesopores and textural mesopores external to the framework-confined mesopores prepared by a method which comprises mixing a neutral amine template and a neutral inorganic oxide precursor, hydrolysis of the precursor with an aqueous solution optionally in the presence of co-solvent to form a gel, aging of the gel to form the crystalline composition, which is then calcined wherein the composition has a particle size of less than about 400 Å, wherein the composition has a $N_2$ adsorption-desorption isotherm with at least one hysteresis loop, wherein the ratio of the textural mesopores to the framework-confined mesopores is above about 0.2, wherein the composition has a specific surface area from about 300 to 1500 m$^2$/g, wherein the composition has a wall thickness of at least 15 Å, wherein crystalline inorganic oxide composition has the formula:

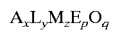

A is optional and is at least one element selected from the group consisting of Ca, Mg, Zn and Cu; L is optional and is at least one element selected from the group consisting of B, Al, Ga, Cr and Fe; M is at least one element selected from the group consisting of Si, Ge, Ti, V, and Zr; E is optional and is at least one element selected from the group consisting of V, W and Mo; O is oxygen and x, y, z, p and q are the molar parts of A, L, M, E and O, respectively, wherein x when present is between 0.001 and 1; y when present is between 0.001 and 2; z when present is between 0.001 and 1; p when present is between 0.001 and 2 and is between 1 and 6 and wherein the composition contains at least one of A, L, and E; and wherein the composition has at least one diffraction pattern selected from the group consisting of FIGS. 2, 3, 7, 8 and 9.

2. The composition of claim 1 wherein L is Al, y is between about 1 and 2 and q is between 1 and 3.

3. The composition of claim 1 having an electron diffraction pattern as shown in FIG. 3.

4. The composition of claim 3 having $N_2$ adsorption-desorption isotherms and Horvath-Kawazoe pore size distribution selected from the group consisting of FIGS. 4A, 4B and 5.

* * * * *

UNITED STATES PATENT AND TRADEMARK OFFICE
CERTIFICATE OF CORRECTION

PATENT NO. : 5,840,264
DATED : November 24, 1998
INVENTOR(S) : Thomas J. Pinnavaia and Peter T. Tanev It is certified that error appears in the above-identified patent and that said Letters Patent is hereby corrected as shown below:

Column 1, line 52, "$\gamma$ or or $\eta$" should be --$\gamma$ or $\eta$--.

Column 4, line 15, " ($C_{12}H_{25}OPO_3$)" should be -- ($C_{12}H_{25}OPO_3^-$)--.

Column 6, line 15, "assess" should be --access--.

Column 6, lines 22 and 23, "This charged" should be --These charged--.

Column 14, line 24, " ($V_1$, cc/g)" should be --($V_t$, cc/g)--.

Column 16, lines 44 and 45, "spacing", second occurrence, should be deleted.

Column 17, line 3, "buthanol" should be --butanol--.

Column 18, lines 49 and 50 (Claim 1), "and is between 1 and 6" should be --and q is between 1 and 6--.

Signed and Sealed this

Fourth Day of May, 1999

Q. TODD DICKINSON

*Attest:*

*Attesting Officer*          *Acting Commissioner of Patents and Trademarks*